United States Patent [19]

Richard et al.

[11] Patent Number: 5,004,594

[45] Date of Patent: Apr. 2, 1991

[54] BENZYLIDENECAMPHOR SULPHONAMIDES DERIVED FROM AMINO ACIDS AND THEIR APPLICATION IN COSMETICS, PARTICULARLY AS SUNSCREENS

[75] Inventors: Herve Richard; Madeleine Leduc, both of Paris; Serge Forestier, Claye Souilly; Gerard Lang, Saint Gratien, all of France

[73] Assignee: L'Oreal, Paris, France

[21] Appl. No.: 287,054

[22] Filed: Dec. 21, 1988

[30] Foreign Application Priority Data

Dec. 22, 1987 [LU] Luxembourg ............................ 87089

[51] Int. Cl.$^5$ ........................ A61K 7/021; A61K 7/40; A61K 7/42; A61K 9/12

[52] U.S. Cl. ............... 424/47; 424/DIG. 5; 424/59; 424/60; 424/61; 424/63; 424/64; 424/70; 514/844; 514/845; 514/846; 514/847; 514/937; 514/938; 514/944

[58] Field of Search ...................... 424/59, 47

[56] References Cited

U.S. PATENT DOCUMENTS

| | | | |
|---|---|---|---|
| 4,775,526 | 10/1988 | Lang et al. ......................... | 424/59 |
| 4,837,006 | 6/1989 | Rosenbaum et al. ................ | 424/59 |

FOREIGN PATENT DOCUMENTS

| | | | |
|---|---|---|---|
| 2309523 | 11/1976 | France ................................ | 424/59 |
| 2025957 | 1/1980 | United Kingdom .................. | 424/59 |
| 2123418 | 2/1984 | United Kingdom .................. | 424/59 |
| 2133984 | 8/1984 | United Kingdom .................. | 424/59 |
| 2151230 | 7/1985 | United Kingdom .................. | 424/59 |

*Primary Examiner*—Dale R. Ore

[57] ABSTRACT

Cosmetic screening composition containing a benzylidene camphor sulphonamide and its use for the protection of human skin against ultraviolet radiation.

15 Claims, No Drawings

BENZYLIDENECAMPHOR SULPHONAMIDES DERIVED FROM AMINO ACIDS AND THEIR APPLICATION IN COSMETICS, PARTICULARLY AS SUNSCREENS

The present invention relates to new sulphonamides derived from 3-benzylidenecamphor and their use in the field of cosmetics, particularly as sunscreens.

It is known that luminous radiations of between 280 and 400 nm enable human skin to tan and that rays of wavelengths between 280 and 320 nm, known under the name of UV-B, cause erythemas and skin burns which may be detrimental to the development of the tanning.

There are already known compounds which are active in the wavelength region 280-320 nm, consisting of 3-benzylidenecamphor derivatives bearing a sulphonic acid or metal or ammonium sulphonate group in position 10 of camphor or in position 3' or 4' of the benzene ring, described in French Patents Nos. 2,282,426 and 2,236,515.

However, while the UV-B rays of wavelengths between 280 and 320 nm play a predominant part in the production of solar erythema and must therefore be filtered out, it nevertheless remains true that UV-A rays of wavelengths between 320 and 400 nm, which make the skin tan, are also capable of inducing a change in the latter, especially in the case of a sensitive skin or of a skin which is continually exposed to solar radiation. In particular, UV-A rays cause a loss of skin elasticity and the appearance of wrinkles, leading to premature aging. They promote the triggering of the erythemateous reaction or intensify this reaction in some individuals and may even be at the source of phototoxic or photoallergic reactions.

It may therefore be advantageous to filter out all the radiation of wavelengths between 280 and 400 nm.

It is known, furthermore, that the constituents forming part of cosmetic preparations do not always have sufficient stability to light and that they degrade under the action of luminous radiations.

Consequently, it is desirable to incorporate in these preparations compounds capable of filtering out UV rays and which, in addition to good screening qualities, must have good stability and sufficient solubility in media which are usually employed in cosmetics.

In the course of its research, the applicants have found new sulphonamides derived from amino acids and from benzylidenecamphor exhibiting good chemical and photochemical stability in addition to good screening power in the wavelength range from 280 to 380 nm. These compounds also exhibit the advantage of not being toxic or irritant and of being perfectly harmless to the skin. Furthermore, the compounds according to the invention endow the cosmetic compositions and especially those for protection against sunlight in which they are employed with good adhesion to skin, and this avoids repeated applications during the exposure to sunlight.

The compounds according to the invention, which are water-soluble or lipid-soluble, exhibit good solubility in the usual cosmetic solvents.

The subject-matter of the present invention is therefore new sulphonamides derived from 3-benzylidenecamphor of general formula:

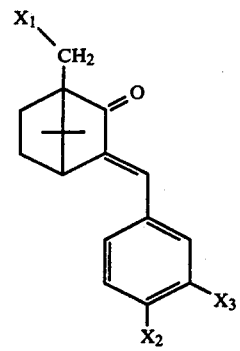 (I)

in which $X_1$ denotes a hydrogen atom or the radical Y, $X_2$ denotes a hydrogen or halogen atom, a $C_1$-$C_4$ alkyl or alkoxy radical or a radical Y or Z, $X_3$ denotes a hydrogen or halogen atom, a $C_1$-$C_4$ alkyl or alkoxy radical or a radical Y or Z, or else $X_2$ and $X_3$ together form an alkylenedioxy group in which the alkylene group contains 1 or 2 carbon atoms, Y denotes a group

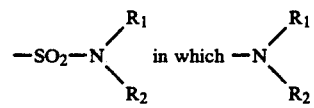

denotes an optionally esterified amino acid residue in which:

$R_1$ and $R_2$ denote a hydrogen atom, an alkyl or hydroxyalkyl group, at least one of these two radicals denoting a group of formula:

(a)

where $R_3$ denotes a hydrogen atom, an alkyl, hydroxyalkyl, amidoalkyl, aminoalkyl, aralkyl, aryl or alkyl group substituted by a heterocyclic ring, or a —($CH_2$)$_n$—COOR$_5$ group with n=1 to 6 but preferably equal to 1 or 2, $R_5$ denoting a hydrogen atom, an alkyl or aralkyl group, $R_3$ may also form with $R_1$ or $R_2$ and the nitrogen atom to which they are attached, a heterocyclic ring such as, for example, a proline or hydroxyproline residue, $R_4$ denotes a hydrogen atom or an alkyl, aralkyl or aryl group, or (b)

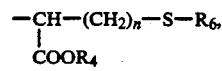

n and $R_4$ having the same values as above and $R_6$ denoting a hydrogen atom or an alkyl, aralkyl or aryl group, or (c)

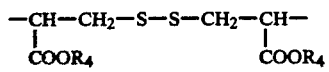

to which two 3-benzylidenecamphor-10-sulphonamide or 3-benzylidenecamphor-3'-sulphonamide or 3-benzylidene-camphor-4'-sulphonamide residues are attached, $R_4$ having the values indicated above, the term "alkyl" denotes straight- or branched-chain $C_1$–$C_{20}$ radicals, the terms "aryl" and "aralkyl" denote non-heterocyclic aromatic radicals of the phenyl and benzyl type and their higher homologues which may be substituted by hydroxy, alkoxy or dialkylamino groups and which may contain 1 to 20 carbon atoms; the term "alkyl substituted by a heterocyclic ring" preferably denotes a histidine or tryptophan residue, $R_4$ may also denote an alkali metal or an $N^{\oplus}(R_7)_4$ group, $R_7$ denoting a hydrogen atom or a $C_1$–$C_4$ alkyl or $C_2$–$C_4$ hydroxyalkyl radical, Z denotes one of the following groups: $Z_1=$

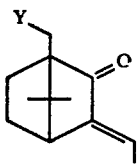

where Y has the meaning referred to above, or $Z_2=$

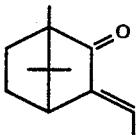

provided that one of the symbols $X_1$, $X_2$ and $X_3$ is different from the other two and that (α) when $X_1$ denotes a hydrogen atom, $X_2$ and $X_3$ are different from each other and cannot assume the value $Z_2$, one of the two having necessarily the value Y or $Z_1$, (β) when $X_1$ has the value Y, $X_2$ and $X_3$ cannot simultaneously assume the value Y or $Z_1$ or $Z_2$, (γ) when $R_1$ or $R_2$ denotes a divalent group of formula (c) in the radical Y, only one of the radicals $X_1$, $X_2$ and $X_3$ may have the value Y and $X_2$ and $X_3$ cannot denote $Z_1$.

When $X_1$ denotes a hydrogen atom and $X_3$ has the value Y, $X_2$ is preferably other than a hydrogen atom.

The process for the preparation of the compounds of formula (I) according to the invention is a two-step process employing, as starting material, the sulphonic acid corresponding to the required sulphonamides, or its alkali metal salt.

The first step consists in preparing the sulphonyl chloride by reacting the starting sulphonic acid or its alkali metal salt with phosphorus pentachloride or with thionyl chloride, optionally in the presence of an inert solvent such as the chlorinated solvents in the conditions described in French Patent 2,529,887. The starting sulphonic acid may be prepared as indicated in French Patents 2,282,426, 2,237,882 and 2,430,938.

In a second step, an amino acid or an ester of an amino acid is reacted with sulphonyl chloride in the presence of an inorganic or organic base to trap the hydrochloric acid which forms, optionally in the presence of an inert solvent such a chlorinated solvents.

When an ester of an amino acid is employed in the second step above, then a hydrolysis of this ester group may be carried out after the condensation reaction with sulphonyl chloride. This hydrolysis may be carried out by means of an alkaline or alkaline-earth base in a solvent such as water or alcohols at a temperature close to the boiling point of the solvent.

Among the amino acids there may be mentioned: glycine, alanine, valine, leucine, isoleucine, phenylalanine, tyrosine, tryptophan, histidine, ornithine, lysine, serine, threonine, cysteine, methionine, aspartic and glutamic acids, asparagine, glutamine, proline, hydroxyproline and cystine.

The preferred amino acids are phenylalanine, tyrosine, glycine, glutamic acid, alanine, cystine and their methyl, ethyl, butyl and tetradecyl esters.

The compounds obtained with an amino acid ester are lipid-soluble, whereas the compounds obtained with an amino acid are water-soluble after the acid functional group is converted into salt with an alkali metal or ammonium hydroxide or an amine such as triethanolamine, diisopropanolamine or 2-amino-2-methyl-1-propanol.

Another subject of the invention is the use in cosmetics of the sulphonamides derived from amino acids and from benzylidenecamphor having the formula (I), especially as agents filtering out the UV rays of wavelengths ranging from 280 to 380 nm.

Another subject of the present invention is the cosmetic compositions containing an effective quantity of at least one compound of formula (I) in a cosmetically acceptable medium and capable of being employed as compositions protecting human skin or hair or as compositions for protection against sunlight.

Another subject of the invention consists of a cosmetic composition, colored or otherwise, stabilized against light, comprising an effective quantity of at least one benzylidenecamphor derivative of the formula (I).

When the compositions according to the invention are employed as compositions intended to protect human skin against ultraviolet rays, they may be in the most diverse forms usually employed in the case of a composition of this type and particularly in the form of oily or alcoholic oil lotions, of emulsions such as a cream or a milk, of alcoholic oil, alcoholic or hydroalcoholic gels, or are packaged as an aerosol or as solid sticks.

They may contain the cosmetic adjuvants usually employed in a composition of this type, such as thickeners, softeners, humectants, surfactants, preservatives, antifoams, perfumes, oils, waxes, lanolin, propellants, colorants and/or pigments, the purpose of which is to color the composition itself or the skin, or any other ingredient usually employed in cosmetics.

The compound of formula (I) is present particularly in proportions by weight of between 0.25 and 3% relative to the total weight of the composition.

The solvent used for solubilizing may be an oil, a wax and, in general, any fatty substance, a monoalcohol, a lower polyol or mixtures thereof. Monoalcohols or polyols which are particularly preferred are ethanol, isopropanol, propylene glycol, glycerine or sorbitol.

An embodiment of the invention is an emulsion in the form of protective cream or milk containing, in addition to the compound of formula (I), fatty alcohols, fatty acid esters such as triglycerides of fatty acids, fatty acids, lanolin, natural and synthetic oils or waxes and emulsifiers, in the presence of water.

Another embodiment consists of oily lotions based on natural or synthetic oils and waxes, of lanolin and of fatty acid esters such as triglycerides of fatty acids and of alcoholic oil lotions based on lower alcohols such as ethanol, or of glycols such as propylene glycol and/or polyols such as glycerine and oils, waxes and fatty acid esters such as the triglycerides of fatty acids.

The cosmetic composition of the invention may also be an alcoholic or hydroalcoholic gel comprising one or more lower alcohols or polyols such as ethanol, propylene glycol or glycerine and a thickener. The alcoholic oil gels additionally contain an oil or a natural or synthetic wax.

The solid sticks consist of natural or synthetic waxes and oils, fatty alcohols, fatty acid esters, lanolin and other fatty substances.

In the case of a composition packaged as an aerosol, traditional propellants such as alkanes, fluoroalkanes and chlorofluoroalkanes are employed.

When the compositions according to the invention are employed as cosmetic compositions for protection against sunlight, they contain at least one compound of formula (I), which may be used in combination, if desired, with another sunscreen specific for the UV-B radiation or the UV-A radiation and compatible with the compounds of formula (I). Two filters according to the invention, one filtering in the UV-B and the other in the UV-A, may be advantageously employed in the compositions for protection against sunlight. A formulation filtering out both UV-B and UV-A rays is thus obtained.

The total quantity of filters in the compositions for protection against sunlight, namely the compound(s) of formula (I) and the other filters if appropriate, is between 0.5 and 15% by weight relative to the total weight of the composition. These compositions for protection against sunlight are in the forms indicated above in the case of the compositions which protect human skin.

By way of sunscreens filtering out the UV-B rays there may be mentioned water-soluble filters such as the benzylidenecamphor derivatives described in the Applicant's French Patents 2,199,971, 2,236,515, 2,282,426 and 2,383,904 and more particularly 4-(2-oxo-3-bornylidenemethyl)phenyltrimethylammonium methyl sulphate, and salts of 4-(2-oxo-3-bornylidenemethyl)benzenesulphonic acid, of 2-methyl-5-(2-oxo-3-bornylidene)benzenesulphonic acid and of 2-phenylbenzimidazole-5-sulphonic acid.

The compounds according to the invention may also be used in combination with UV-B filters consisting of lipid-soluble compounds or of oils having screening properties such as, in particular, coffee oil. By way of lipophile UV-B sunscreens there maY be mentioned esters of salicylic acid such as 2-ethylhexyl salicylate, homomenthyl salicylate, esters of cinnamic acid such as 2-ethylhexyl p-methoxycinnamate or 2-ethoxyethyl p-methoxycinnamate, esters of p-aminobenzoic acid such as amyl p-aminobenzoate or 2-ethylhexyl p-dimethylaminobenzoate, benzophenone derivatives such as 2-hydroxy-4-methoxybenzophenone or 2,2'-dihydroxy-4-methoxybenzophenone, camphor derivatives such as 3-(4'-methylbenzylidene)camphor or 3-benzylidenecamphor, and dialkyl benzalmalonates such as di-2-ethylhexyl 4'-methoxybenzalmalonate.

The compounds according to the invention may also be used in combination with UV-A filters among which there may be mentioned dibenzoylmethane derivatives such as those described in French Patent Application 2,440,933 and German Patent Application 2,544,180.

It is to be understood that the list of sunscreens employed in combination with the compounds (I) according to the invention, which is indicated above does not constitute a limitation.

The present invention is also aimed at a process for protecting cosmetic compositions colored or otherwise, consisting in incorporating in these compositions an effective quantity of at least one compound of formula (I) as an agent for protection against ultraviolet rays.

These compositions may consist of hair-care compositions such as hair lacquers, hair setting lotions which may be conditioning or disentangling if desired, shampoos, coloring shampoos, make-up products such as nail varnishes, skin treatment creams, foundations, lipsticks, and any other cosmetic composition capable, because of its constituents, of presenting problems of stability to light during storage. Such compositions contain 0.1 to 3% by weight of the compound of formula (I).

A further subject-matter of the present invention is a process for protecting the skin against UV radiation consisting in applying to the skin an effective quantity of at least one compound of formula (I) present in a cosmetically acceptable carrier.

The invention is illustrated by the examples below, which do not imply any limitation.

By way of compounds (I) according to the invention there may be mentioned, for example, compounds of Examples 1 to 10, whose preparative method and various characteristics [appearance, wavelength corresponding to maximum absorption ($\lambda_{max}$), molecular extinction coefficient ($\epsilon$) and elemental analysis] are indicated in the table below.

| Example | x₁ | x₂ | x₃ | Melting point | UV spectrum (95° EtOH) ν max (nm) | ε | Elemental analysis Calculated (%) | Found (%) |
|---|---|---|---|---|---|---|---|---|
| Ex. 1 | H | CH₃ | —SO₂—NH—CH—CH₂—C₆H₅<br>                                     CO₂C₁₄H₂₉ | oil | 293 | 22000 | $C_{41}H_{59}NO_5S·0.4H_2O$<br>C 71.82<br>H 8.73<br>N 2.04<br>O 12.59<br>S 4.67 | 71.82<br>8.08<br>2.04<br>12.41<br>4.63 |
| Ex. 2 | H | CH₃ | —SO₂NH—CH—CH₂—C₆H₄—OH<br>             CO₂CH₃ | 176° C. | 292 | 22800 | $C_{28}H_{33}NO_6S$<br>C 65.72<br>H 6.50<br>N 2.74<br>O 18.78<br>S 6.27 | 65.52<br>6.57<br>2.71<br>19.21<br>5.65 |
| Ex. 3 | H | —SO₂NHCH₂CO₂C₄H₉ | H | viscous oil | 294 | 25600 | $C_{23}H_{31}NO_5S$<br>C 63.71<br>H 7.21<br>N 3.23<br>O 18.78<br>S 7.39 | 63.56<br>7.18<br>3.16<br>7.18 |
| Ex. 4 | H | CH₃ | —SO₂NH—CH—(CH₂)₂CO₂C₂H₅<br>             CO₂C₂H₅ | 95° C. | 293 | 25400 | $C_{27}H_{37}NO_7S$<br>C 62.40<br>H 7.18<br>N 2.69<br>O 21.55<br>S 6.17 | 62.50<br>7.19<br>2.64<br>21.45<br>5.95 |
| Ex. 5 | —SO₂—NH—CH—CO₂C₂H₅<br>           CH₃ | | —O—Cl₂—O— | 90° C. | 338 | 19450 | $C_{23}H_{29}NO_7S$<br>C 59.59<br>H 6.30<br>N 3.02<br>O 24.17<br>S 6.92 | 59.39<br>6.33<br>2.80<br>24.21<br>6.79 |
| Ex. 6 | ⟨SO₂—NH—CH—CH₂—S⟩₇<br>           CO₂CH₃ | | —O—CH₂—O— | 107° C. | 337 | 39400 | $C_{44}H_{52}N_2O_{14}S_4$<br>C 54.98<br>H 5.45<br>N 2.91<br>O 23.30<br>S 13.33 | 54.61<br>5.54<br>2.82<br>23.72<br>13.01 |
| Ex. 7 | —SO₂—NH—CH—CH₂—C₆H₅<br>           CO₂C₁₄H₂₉ | —OCH₃ | H | oil | 323 | 28450 | $C_{41}H_{59}NO_6S$<br>C 70.90<br>H 8.57<br>N 2.02<br>O —<br>S 4.62 | 70.74<br>8.62<br>2.05<br>—<br>4.79 |

-continued

| Example | x1 | x2 | x3 | Melting point | UV spectrum (95° EtOH) ν max (nm) | ε | Elemental analysis Calculated (%) | Found (%) |
|---|---|---|---|---|---|---|---|---|
| Ex. 8 | H | CH₃ | —SO₂—NH—CH—(CH₂)₂CO₂H<br>\|<br>CO₂H | softens at, about 143° C. | 293 | 23550 | $C_{21}H_{29}NO_7S$<br>C 59.59<br>H 6.30<br>O 24.16<br>S 6.92<br>N 3.02 | 59.76<br>6.38<br>24.13<br>6.76<br>2.97 |
| Ex. 9 | —SO₂—NHCH₂CO₂C₂H₅ | H | H | 85° C. | 293 | 23000 | $C_{21}H_{27}NO_5S$<br>C 62.20<br>H 6.71<br>N 3.45<br>S 7.91 | 62.07<br>6.83<br>3.99<br>7.79 |
| Ex. 10 | —SO₂—NHCH₂CO₂H | H | H | 195° C. | 293 | 22500 | $C_{19}H_{23}NO_5S$<br>C 60.46<br>H 6.14<br>N 3.71<br>S 8.49 | 60.28<br>6.15<br>3.64<br>8.35 |

The compound of Example 3 is prepared in the following manner:

(1) Preparation of n-butyl glycinate methanesulphonate

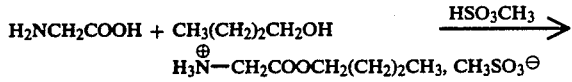

A mixture of 0.2 mole (15.01 g) of glycine and 0.5 mole (37.06 g) of n-butanol is heated to 100° C.

0.28 mole (18.2 ml) of methanesulphonic acid is introduced dropwise into the mixture.

After 6 hours' stirring at 104° C., the reaction mixture is poured into 1 liter of isopropyl ether. The oil is stirred and is allowed to deposit and then settle in the ether. This operation is repeated once. The oil is then dried under vacuum. 44.5 g of colorless oil are recovered; the yield is therefore 97%.

(2) Preparation of the sulchonamide

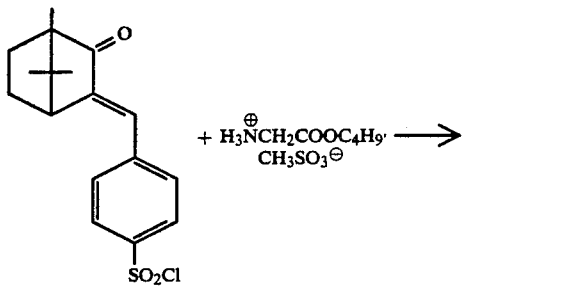

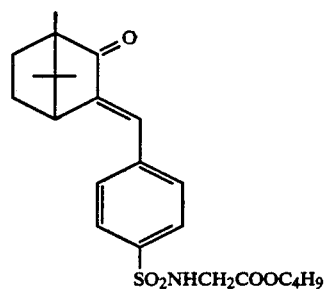

0.033 mole (11.17 g) of 4-(2-oxo-3-bornylidenemethyl)benzenesulphonyl chloride is added dropwise at reflux to a solution of 0.03 mole (6.82 g) of butyl glycinate salt, 120 ml of anhydrous dichloromethane and 0.075 mole of triethylamine (10.5 ml).

The reaction mixture is refluxed for 2 hours.

The triethylamine salt is filtered off. The filtrate is washed with water, is dried over sodium sulphate and is then concentrated under vacuum.

After a chromatography under pressure with dichloromethane as eluent, 10.9 g of pale yellow oil are recovered, that is an 84% yield.

The results of elemental analysis indicated in the above table show that the required product is, in fact, obtained.

The compounds in the other examples are prepared in a similar manner from the corresponding amino acids.

The compounds (I) according to the invention may be introduced into the following cosmetic compositions:

EXAMPLES OF FORMULATION

EXAMPLE 1

Sunlight protection oil

The following constituents are heated to about 40°–45° C. in order to obtain a homogeneous composition:

| | |
|---|---|
| Compound of Example 1 | 2.5 g |
| Triglycerides of $C_8$–$C_{12}$ fatty acids "Miglyol 812" (Dynamit Nobel) | 20 g |
| Sunflower oil | 20 g |
| Synthetic oil of formula $C_{15}H_{31}COO-CH_2-CH-CH_2-O-CH_2-CH-C_4H_9$ with OH and $C_2H_5$ substituents | 10 g |
| Perfume | 1.2 g |
| Cyclic dimethyl polysiloxane "Volatile Silicone 7207" (Union Carbide) q.s. | 100 g |

EXAMPLE 2

O/W sunlight protection cream

| | |
|---|---|
| Compound of Example 4 | 2 g |
| Compound of Example 9 | 1 g |
| Cetylstearyl alcohol with 15 moles of ethylene oxide = "Mergital CS15" (Henkel-France) | 2.6 g |
| Mixture of glycerol mono- and distearate: "Geleol Copeaux" (Gattefosse) | 5 g |
| Stearyl alcohol | 4 g |
| Glycerine | 5 g |
| Preservative | 0.2 g |
| Perfume | 0.6 g |
| Demineralized water | q.s. 100 g |

The filters are dissolved in the fatty phase, which is heated to about 75°–80° C. The aqueous phase containing the glycerine and the emulsifier is heated to about 75–80° C. with vigorous stirring; the fatty phase is added to the aqueous phase and cooling is allowed to take place with moderate stirring. The perfume and the preservative are added at about 40° C.

EXAMPLE 3

W/O sunlight protection cream

| | |
|---|---|
| Compound of Example 3 | 3 g |
| Glycerine and sorbitan esters of fatty acids "Arlacel 481" (Atlas) | 6.5 g |
| Triglycerides of $C_8$–$C_{12}$ fatty acids "Miglyol 812" (Dynamit Nobel) | 20 g |
| Benzoate of $C_{12}$–$C_{15}$ alcohols "Finsolv TN" (Finetex) | 5 g |
| Propylene glycol | 2 g |
| Magnesium sulphate with 7 molecules of water | 1 g |
| Preservative | 0.2 g |
| Perfume | 0.6 g |
| Demineralized water | q.s. 100 g |

The filter is dissolved in the fatty phase containing the emulsifier, which is heated to about 75°–80° C.

The aqueous phase containing the propylene glycol is heated to about 75°–80° C. and the aqueous phase is added to the fatty phase with vigorous stirring. Cooling is allowed to take place with moderate stirring and the perfume and the preservative are added to about 40° C.

We claim:

1. A cosmetic sunscreening composition for protecting the skin and hair from ultraviolet rays, said composition comprising in a cosmetically acceptable medium and in an amount effective to protect the hair and skin from ultraviolet rays, at least one sulphonamide derived from 3-benzylidenecamphor and having the formula

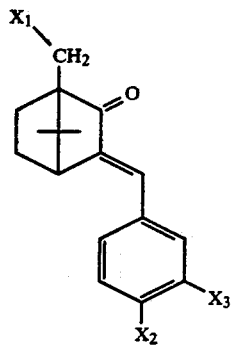

(I)

wherein
$X_1$ represents hydrogen or Y,
$X_2$ represents hydrogen, halogen, $C_1$-$C_4$ alkyl, $C_1$-$C_4$ alkoxy, Y or Z,
$X_3$ represents hydrogen, halogen, $C_1$-$C_4$ alkyl, $C_1$-$C_4$ alkoxy, Y or Z,
or $X_2$ and $X_3$ together form an alkylenedioxy group wherein the alkylene moiety contains 1 or 2 carbon atoms,
Y represents

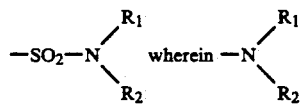

represents an amino acid residue, esterified or not, wherein
$R_1$ and $R_2$ represent hydrogen, alkyl or hydroxyalkyl, with the proviso that at least one of $R_1$ and $R_2$ represents:

(a)

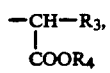

wherein $R_3$ represents hydrogen, alkyl, hydroxyalkyl, amidoalkyl, aminoalkyl, aralkyl, aryl or alkyl substituted by a heterocyclic ring, or —$(CH_2)_n$—$COOR_5$ wherein n is 1 to 6 and $R_5$ represents hydrogen, alkyl or aralkyl or $R_3$ together with $R_1$ or $R_2$ and the nitrogen atom to which they are attached form a heterocyclic ring, and $R_4$ represents hydrogen, alkyl, aralkyl or aryl, (b)

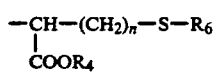

wherein n and $R_4$ have the meanings given above and
$R_6$ represents hydrogen, alkyl, aralkyl or aryl, or (c)

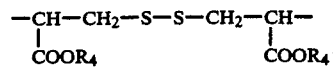

to which two 3-benzylidenecamphor-10-sulphonamide or 3-benzylidenecamphor-3'-sulphonamide or 3-benzylidenecamphor-4'-sulphonamide residues are attached,
$R_4$ has the meaning given above or an alkali metal or $N^+(R_7)$ wherein $R_7$ represents hydrogen, $C_1$-$C_4$ alkyl or $C_2$-$C_4$ hydroxyalkyl,
Z represents one of the following
(a) $Z_1$ which has the formula

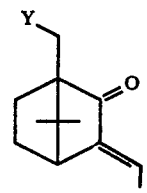

wherein Y has the meaning given above, or
(b) $Z_2$ which has the formula

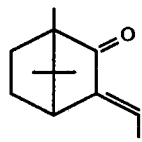

with the proviso that one of $X_1$, $X_2$ and $X_3$ is different from the other two and that
($\alpha$) when $X_1$ represents hydrogen, $X_2$ and $X_3$ are different from each other and cannot be $Z_2$, one of the two necessarily being Y or $Z_1$,
($\beta$) when $X_1$ represents Y, $X_2$ and $X_3$ are not simultaneously Y or $Z_1$ or $Z_2$, and
($\gamma$) when $R_1$ or $R_2$ represents a divalent group of formula (c) in the radical Y, only one of $X_1$, $X_2$ and $X_3$ can be Y, and $X_2$ and $X_3$ cannot be $Z_1$, and in the above,
alkyl represents a straight or branched chain $C_1$-$C_{20}$ radical,
aryl represents phenyl or a higher homologue thereof unsubstituted or substituted by hydroxy, alkoxy or dialkylamino and which contains 1-20 carbon atoms,
aralkyl represents benzyl or a higher homologue thereof unsubstituted or substituted by hydroxy, alkoxy or dialkylamino and which contains 1-20 carbon atoms, and
alkyl substituted by a heterocyclic ring represents a histidine or tryptophan residue.

2. The cosmetic composition of claim 1 wherein in said sulphonamide derived from 3-benzylidenecamphor having formula (I), $X_1$ represents hydrogen, $X_2$ represents methyl and $X_3$ is selected from the group consisting of (i) 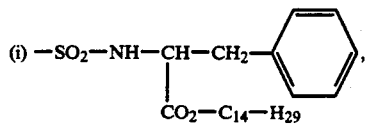

-continued (ii) 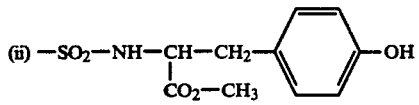

and (iii) 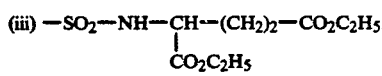

3. The cosmetic composition of claim 1 wherein in said sulphonamide derived from 3-benzylidenecamphor having formula (I), $X_2$ and $X_3$ represent methylenedioxy and $X_1$ represents (i) 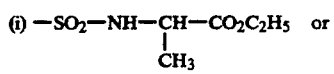 or (ii) 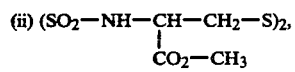, the divalent radical (ii) being attached to two 3-benzylidenecamphor residues bearing a methylenedioxy group in positions 3' and 4'.

4. The cosmetic composition of claim 1 wherein in said sulphonamide derived from 3-benzylidene camphor having formula (I), $X_1$ represents

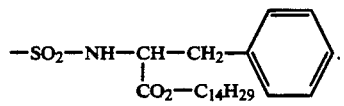

5. The cosmetic composition of claim 1 wherein in said sulphonamide derived from 3-benzylidenecamphor having formula (I), $X_2$ and $X_3$ simultaneously represent hydrogen and $X_1$ is selected from the group consisting of $-SO_2-NH-CH_2-CO_2-C_2H_5$ and $-SO_2-NH-CH_2-CO_2H$.

6. The cosmetic composition of claim 1 wherein in said sulphonamide derived from 3-benzylidenecamphor having formula (I), $X_1$ and $X_3$ represent hydrogen and $X_2$ represents $-SO_2NHCH_2CO_2C_4H_9$.

7. The cosmetic composition of claim 1 in a form selected from the group consisting of an oily gel lotion, an alcoholic oil lotion, an emulsion, an alcoholic oil, an alcoholic gel, a hydroalcoholic gel, a solid stick or an aerosol.

8. The cosmetic composition of claim 1 in the form of an emulsion.

9. The cosmetic composition of claim 1 wherein said sulphonamide derived from 3-benzylidenecamphor having formula (I) is present in an amount ranging from 0.5 to 15 percent by weight based on the total weight of said composition.

10. The cosmetic composition of claim 1 which also contains, in addition to said sulphonamide derived from 3-benzylidenecamphor having formula (I), at least one of (i) a water-soluble or lipid-soluble sunscreen having filtering action toward UV-B rays selected from the group consisting of a benzylidene camphor derivative, coffee oil, salicylic acid ester, cinnamic acid ester, p-aminobenzoic acid ester, a benzophenone derivative, a dialkyl benzalmalonate and (ii) a dibenzoylmethane UV-A sunscreen.

11. The cosmetic composition of claim 1 in the form of a composition for protecting human skin, said sulphonamide derived from 3-benzylidenecamphor having formula (I) being present in an amount ranging from 0.25 to 3 percent by weight based on the total weight of said composition.

12. The cosmetic composition of claim 1 which also contains at least one cosmetic adjuvant selected from the group consisting of a thickener, a softener, a humectant, a surfactant, a preservative, an anti-foam agent, a perfume, an oil, a wax, lanolin, a lower monoalcohol, a polyol, a propellant, a colorant and a pigment.

13. The cosmetic composition of claim 1 wherein said sulphonamide derived from 3-benzylidenecamphor having formula (I) is present in an amount ranging from 0.1 to 3 percent by weight based on the total weight of said composition.

14. A process for protecting human skin against ultraviolet rays comprising applying to said skin in an amount to protect said skin from said ultraviolet rays a cosmetic sunscreening composition comprising in a cosmetically acceptable medium at least one sulphonamide derived from 3-benzylidenecamphor and having the formula

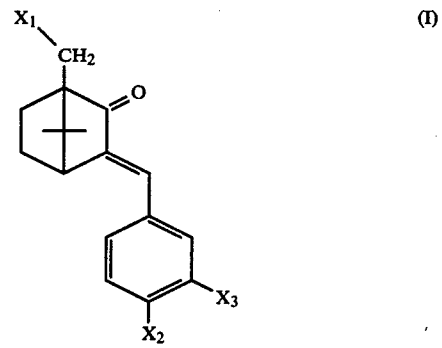 (I)

$X_1$ represents hydrogen or Y, $X_2$ represents hydrogen, halogen, $C_1-C_4$ alkyl, $C_1-C_4$ alkoxy, Y or Z, $X_3$ represents hydrogen, halogen, $C_1-C_4$ alkyl, $C_1-C_4$ alkoxy, Y or Z, or $X_2$ and $X_3$ together form an alkylenedioxy group wherein the alkylene moiety contains 1 or 2 carbon atoms, Y represents

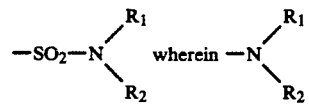

represents an amino acid residue, esterified or not, wherein $R_1$ and $R_2$ represent hydrogen, alkyl or hydroxyalkyl, with the proviso that at least one of $R_1$ and $R_2$ represents:

(a)

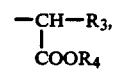

wherein $R_3$ represents hydrogen, alkyl, hydroxyalkyl, amidoalkyl, aminoalkyl, aralkyl, aryl or alkyl substituted by a heterocyclic ring, or —$(CH_2)_n$—$COOR_5$ wherein n is 1 to 6 and $R_5$ represents hydrogen, alkyl or aralkyl or $R_3$ together with $R_1$ or $R_2$ and the nitrogen atom to which they are attached form a heterocyclic ring, and $R_4$ represents hydrogen, alkyl, aralkyl or aryl, (b)

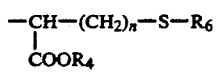

wherein n and $R_4$ have the meanings given above and $R_6$ represents hydrogen, alkyl, aralkyl or aryl, or (c)

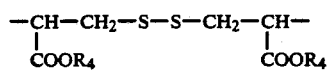

to which two 3-benzylidenecamphor-10-sulphonamide or 3-benzylidenecamphor-3'-sulphamide or 3-benzylidenecamphor-4'-sulphamide residues are attached, $R_4$ has the meaning given above or an alkali metal or $N^+(R_7)$ wherein $R_7$ represents hydrogen, $C_1$–$C_4$ alkyl or $C_2$–$C_4$ hydroxyalkyl, Z represent one of the following (a) $Z_1$ which has the formula

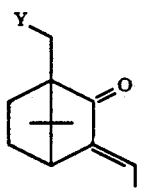

wherein Y has the meaning given above, or (b) $Z_2$ which has the formula

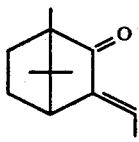

with the proviso that one of $X_1$, $X_2$ and $X_3$ is different from the other two and that (α) when $X_1$ represents hydrogen, $X_2$ and $X_3$ are different from each other and cannot be $Z_2$, one of the two necessarily being Y or $Z_1$, (β) when $X_1$ represents Y, $X_2$ and $X_3$ are not simultaneously Y or $Z_1$ or $Z_2$, and (γ) when $R_1$ or $R_2$ represents a divalent group of formula (c) in the radical Y, only one of $X_1$, $X_2$ and $X_3$ can be Y, and $X_2$ and $X_3$ cannot be $Z_1$, and in the above, alkyl represents a straight or branched chain $C_1$–$C_{20}$ radical, aryl represents phenyl or a higher homologue thereof unsubstituted or substituted by hydroxy, alkoxy or dialkylamino and which contains 1–20 carbon atoms, aralkyl represents benzyl or a higher homologue thereof unsubstituted or substituted by hydroxy, alkoxy or dialkylamino and which contains 1–20 carbon atoms, and alkyl substituted by a heterocyclic ring represents a histidine or tryptophan residue.

15. A process for protecting a cosmetic composition against UV rays comprising incorporating into said cosmetic composition in an amount effective to protect said composition against UV rays, at least on sulphonamide derived from 3-benzylidenecamphor and having the formula

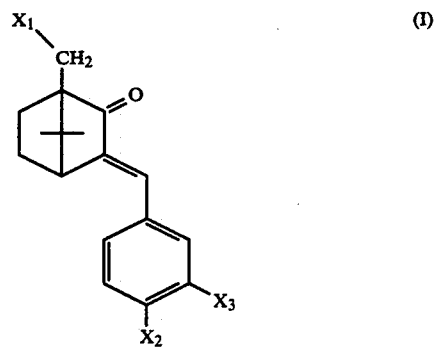

wherein $X_1$ represents hydrogen or Y, $X_2$ represents hydrogen, halogen, $C_1$–$C_4$ alkyl, $C_1$–$C_4$ alkoxy, Y or Z, $X_3$ represents hydrogen, halogen, $C_1$–$C_4$ alkyl, $C_1$–$C_4$ alkoxy, Y or Z, or $X_2$ and $X_3$ together form an alkylenedioxy group wherein the alkylene moiety contains 1 or 2 carbon atoms, Y represents

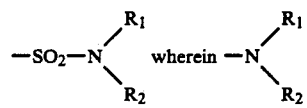

represents an amino acid residue, esterified or not, wherein $R_1$ and $R_2$ represent hydrogen, alkyl or hydroxyalkyl, with the proviso that at least one of $R_1$ and $R_2$ represents:

(a)

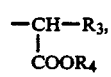

wherein $R_3$ represents hydrogen, alkyl, hydroxyalkyl, amidoalkyl, aminoalkyl, aralkyl, aryl or alkyl substituted by a heterocyclic ring, or —$(CH_2)_n$—$COOR_5$ wherein n is 1 to 6 and $R_5$ represents hydrogen, alkyl or aralkyl or $R_3$ together with $R_1$ or $R_2$ and the nitrogen atom to which they are attached form a heterocyclic ring, and $R_4$ represents hydrogen, alkyl, aralkyl or aryl, (b)

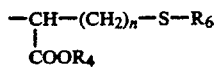

wherein n and $R_4$ have the meanings given above and $R_6$ represents hydrogen, alkyl, aralkyl or aryl, or (c)

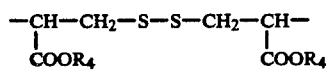

to which two 3-benzylidenecamphor-10-sulphonamide or 3-benzylidenecamphor-3'-sulphonamide or 3-benzylidenecamphor-4'-sulphonamide residues are attached, $R_4$ has the meaning given above or an alkali metal or $N^+(R_7)$ wherein $R_7$ represents hydrogen, $C_1$-$C_4$ alkyl or $C_2$-$C_4$ hydroxyalkyl, Z represents one of the following (a) $Z_1$ which has the formula

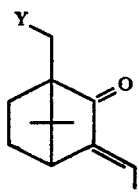

wherein Y has the meaning given above, or (b) $Z_2$ which has the formula

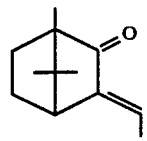

with the proviso that one of $X_1$, $X_2$ and $X_3$ is different from the other two and that (α) when $X_1$ represents hydrogen, $X_2$ and $X_3$ are different from each other and cannot be $Z_2$, one of the two necessarily being Y or $Z_1$, (β) when $X_1$ represents, Y, $X_2$ and $X_3$ are not simultaneously Y or $Z_1$ or $Z_2$, and (γ) when $R_1$ or $R_2$ represents a divalent group of formula (c) in the radical Y, only one of $X_1$, $X_2$ and $X_3$ can be Y, and $X_2$ and $X_3$ cannot be $Z_1$, and in the above, alkyl represents a straight or branched chain $C_1$-$C_{20}$ radical, aryl represents phenyl or a higher homologue thereof unsubstituted or substituted by hydroxy, alkoxy or dialkylamino and which contains 1-20 carbon atoms, aralkyl represents benzyl or a higher homologue thereof unsubstituted or substituted by hydroxy, alkoxy or dialkylamino and which contains 1-20 carbon atoms, and alkyl substituted by a heterocyclic ring represents a histidine or tryptophan residue.

* * * * *